(12) United States Patent
Messerchmidt

(10) Patent No.: US 8,730,468 B2
(45) Date of Patent: May 20, 2014

(54) METHODS, DEVICES AND KITS FOR PERI-CRITICAL REFLECTANCE SPECTROSCOPY

(75) Inventor: Robert G. Messerchmidt, Los Altos, CA (US)

(73) Assignee: Rare Light, Inc., Mountain View, CA (US)

( * ) Notice: Subject to any disclaimer, the term of this patent is extended or adjusted under 35 U.S.C. 154(b) by 180 days.

(21) Appl. No.: 12/865,698

(22) PCT Filed: Jan. 30, 2009

(86) PCT No.: PCT/US2009/032706
§ 371 (c)(1),
(2), (4) Date: Jul. 30, 2010

(87) PCT Pub. No.: WO2009/137122
PCT Pub. Date: Nov. 12, 2009

(65) Prior Publication Data
US 2011/0001965 A1    Jan. 6, 2011

Related U.S. Application Data

(60) Provisional application No. 61/025,737, filed on Feb. 1, 2008.

(51) Int. Cl.
*G01J 3/44* (2006.01)
(52) U.S. Cl.
USPC ........................................................ 356/300
(58) Field of Classification Search
USPC ........................................................ 356/300
See application file for complete search history.

(56) References Cited

U.S. PATENT DOCUMENTS

| | | | |
|---|---|---|---|
| 4,692,024 A * | 9/1987 | Bloss | 356/135 |
| 4,730,882 A | 3/1988 | Messerschmidt et al. | |

(Continued)

FOREIGN PATENT DOCUMENTS

| | | | |
|---|---|---|---|
| CN | 1629618 A | 6/2005 | |
| CN | 1749735 A | 3/2006 | |

(Continued)

OTHER PUBLICATIONS

"International Application Serial No. PCT/US2009/032706, International Search Report mailed Nov. 27, 2009", 2 pgs.

(Continued)

*Primary Examiner* — Tu Nguyen
(74) *Attorney, Agent, or Firm* — Schwegman Lundberg & Woessner, P.A.

(57) ABSTRACT

Spectroscopy apparatuses oriented to the critical angle of the sample are described that detect the spectral characteristics of a sample. The apparatus includes an electromagnetic radiation source adapted to excite a sample with electromagnetic radiation introduced to a measurement site of the sample at a plurality of angles of incidence near a critical angle of the sample and a transmitting crystal in communication with the electromagnetic radiation source and the sample. The transmitting crystal may have a high refractive index adapted to reflect the electromagnetic radiation internally. The apparatus includes a reflector adapted to introduce the electromagnetic radiation to a measurement site of the sample at a plurality of angles of incidence near the critical angle between the transmitting crystal and sample. The apparatus includes a detector for detecting the electromagnetic radiation from the sample. Also, provided herein are methods, systems, and kits incorporating the peri-critical reflectance spectroscopy apparatus.

31 Claims, 5 Drawing Sheets

(56) References Cited

U.S. PATENT DOCUMENTS

| | | | |
|---|---|---|---|
| 5,229,833 | A | 7/1993 | Stewart |
| 5,946,083 | A | 8/1999 | Melendez et al. |
| 6,141,100 | A | 10/2000 | Burka et al. |
| 6,362,144 | B1 | 3/2002 | Berman et al. |
| 6,417,924 | B1 | 7/2002 | Kimura |
| 6,430,424 | B1 | 8/2002 | Berman et al. |
| 6,462,809 | B1 | 10/2002 | Ryan et al. |
| 6,493,080 | B1 | 12/2002 | Boese |
| 6,493,097 | B1 | 12/2002 | Ivarsson |
| 6,748,250 | B1 | 6/2004 | Berman et al. |
| 6,841,792 | B2 | 1/2005 | Bynum et al. |
| 6,862,094 | B2 | 3/2005 | Johansen |
| 6,906,327 | B2 * | 6/2005 | Shelley et al. ........... 250/339.01 |
| 6,908,773 | B2 | 6/2005 | Ii et al. |
| 6,992,770 | B2 * | 1/2006 | Naya ............................ 356/445 |
| 7,460,236 | B2 | 12/2008 | Ivarsson |
| 2005/0229698 | A1 | 10/2005 | Beecroft |
| 2006/0043301 | A1 | 3/2006 | Mantele et al. |
| 2006/0134669 | A1 | 6/2006 | Casasanta, III |
| 2006/0164633 | A1 | 7/2006 | Koshoubu et al. |
| 2006/0165633 | A1 | 7/2006 | Nguyen et al. |
| 2006/0187459 | A1 | 8/2006 | Ok et al. |
| 2007/0013912 | A1 | 1/2007 | Ivarsson |
| 2007/0081163 | A1 | 4/2007 | Liang et al. |
| 2010/0259254 | A1 | 10/2010 | Verschuren et al. |
| 2011/0001965 | A1 | 1/2011 | Messerschmidt |
| 2011/0188030 | A1 | 8/2011 | Verschuren et al. |
| 2012/0088486 | A1 | 4/2012 | Messerchmidt |

FOREIGN PATENT DOCUMENTS

| | | |
|---|---|---|
| JP | 04282435 A | 10/1992 |
| JP | 06288902 A | 10/1994 |
| JP | 11132941 A | 5/1999 |
| JP | 1999132941 | 5/1999 |
| JP | 2000-180353 A | 6/2000 |
| JP | 2000180353 A | 6/2000 |
| JP | 2001-511249 A | 8/2001 |
| JP | 2002162346 A | 6/2002 |
| JP | 2002174591 A | 6/2002 |
| JP | 2002530643 A | 9/2002 |
| JP | 2004500571 A | 1/2004 |
| JP | 2005241278 A | 9/2005 |
| JP | 2006201163 A | 8/2006 |
| JP | 2006317349 A | 11/2006 |
| JP | 2007127670 A | 5/2007 |
| JP | 2010156556 A | 7/2010 |
| JP | 2011511292 A | 4/2011 |
| KR | 1020040067322 A | 7/2004 |
| KR | 1020060020036 A | 3/2006 |
| KR | 10-0628877 B1 | 9/2006 |
| KR | 10-0668323 B1 | 1/2007 |
| WO | WO-2007121406 A2 | 10/2007 |
| WO | WO-2009/137122 A1 | 11/2009 |
| WO | WO-2009137122 A2 | 11/2009 |
| WO | WO-2010118175 A2 | 10/2010 |
| WO | WO-2010118175 A3 | 10/2010 |
| WO | WO-2012149343 A1 | 11/2012 |

OTHER PUBLICATIONS

"Australian Application Serial No. 2010234465, First Examination Report mailed Aug. 14, 2012", 2 pgs.
"Chinese Application Serial No. 200980112418.9, Response filed Jul. 19, 2012 to Office Action mailed Jan. 5, 2012", With English Claims, 11 pgs.
"Chinese Application Serial No. 2009801124189, Office Action mailed Jan. 5, 2012", With English Translation, 14 pgs.
"International Application Serial No. PCT/US2010/030299, International Preliminary Report on Patentability mailed Oct. 20, 2011", 5 pgs.
"International Application Serial No. PCT/US2010/030299, International Search Report mailed Jan. 31, 2011", 5 pgs.
"International Application Serial No. PCT/US2010/030299, Written Opinion mailed Jan. 31, 2011", 3 pgs.
"Korean Application Serial No. 10-2010-7019454, Office Action mailed May 14, 2012", KR Translation Only, 10 pgs.
"Chinese Application Serial No. 200980112418.9, Office Action mailed Nov. 28, 2012", 32 pgs.
"International Application No. PCT/US2012/035484, International Search Report mailed Aug. 23, 2012", 6 pgs.
"International Application No. PCT/US2012/035484, Written Opinion mailed Aug. 23, 2012", 8 pgs.
"Japanese Application Serial No. 2010-545225, Office Action mailed Dec. 20, 2012", 6 pgs.
"Korean Application Serial No. 10-2011-7026540, Notice of Preliminary Rejection mailed Nov. 30, 2012", 3 pgs.
Fontaine, N. H, et al., "Variable-angle internal-reflection Raman spectroscopy for depth-resolved vibrational characterization of polymer thin films", Phys. Rev. B, 57, (1998), 3807-3810.
Greene, P. R, et al., "Total internal reflection Raman spectroscopy of barley leaf epicuticular waxes in vivo", Colloids and Surfaces B: Biointerfaces, 45(3-4), (Nov. 10, 2005), 174-180.
Holzer, W., et al., "Raman study on surface layers and thin films by using total reflection experiments", Journal of Molecular Structure, 217, (Mar. 1990), 253-264.
Ishizaki, Fumihiko, et al., "Near-Infrared Attenuated Total Reflection Raman Spectroscopy for Polymer Surface Observation", Japanese Journal of Applied Physics, 47, (2008), 1621-1627.
McKee, K., et al., "Development of a scanning angle total internal reflection Raman spectrometer", Review of Scientific Instruments, 81(4), (2010), 043106.
"Chinese Application Serial No. 200980112418.9, Office Action mailed Jun. 19, 2013", 10 pgs.
"Chinese Application Serial No. 200980112418.9, Response filed Feb. 16, 2013 to Office Action mailed Nov. 28, 2012", 12 pgs.
"Korean Application Serial No. 10-2010-7019454, Amended Claims filed Feb. 15, 2013", 9 pgs.
"Korean Application Serial No. 10-2010-7019454, Appeal Brief filed Mar. 19, 2013", 13 pgs.
"Korean Application Serial No. 10-2010-7019454, Notice of Final Rejection mailed Jan. 16, 2013", 3 pgs.
"Korean Application Serial No. 10-2010-7019454, Office Action mailed Jul. 31, 2013", 23 pgs.
"Japanese Application Serial No. 2012-504837, Office Action mailed Dec. 4, 2013", 4 pgs.
"Australian Application Serial No. 2012249441, Amendment filed Sep. 27, 2013", 9 pgs.
"Chinese Application Serial No. 200980112418.9, Response filed Nov. 4, 2013 to Office Action mailed Jun. 19, 2013", 12 pgs.
"Chinese Application Serial No. 201080025328.9, Office Action mailed Aug. 21, 2013", 10 pgs.
"International Application Serial No. PCT/US2012/035484, International Preliminary Report on Patentability mailed Nov. 7, 2013", 8 pgs.
"Korean Application Serial No. 10-2011-7026540, Office Action mailed Aug. 20, 2013", 11 pgs.
"U.S. Appl. No. 13/098,140, Non Final Office Action mailed Feb. 12, 2014", 13 pgs.
"Japanese Application Serial No. 2010-545225, Office Action mailed Jan. 29, 2014", (W/ English Translation), 7 pgs.

* cited by examiner

METHODS, DEVICES AND KITS FOR PERI-CRITICAL REFLECTANCE SPECTROSCOPY

CROSS-REFERENCE TO CLAIM OF PRIORITY

This patent application is a U.S. National Stage Filing under 35 U.S.C. 371 from International Patent Application Serial No. PCT/US2009/032706, filed Jan. 30, 2009 and published on Nov. 12, 2009 as WO 2009/137122 A9, which claims the benefit of priority to U.S. Provisional Application No. 61/025,737, filed Feb. 1, 2008, the contents of which are incorporated herein by reference in their entirety.

BACKGROUND OF THE INVENTION

Internal reflection spectroscopy, also known as Attenuated Total Reflectance (ATR) spectroscopy, has been know for many years, and is a widely used method of sampling in infrared (IR) and fluorescence spectroscopy, as well as in other spectroscopies. Mid-wavelength infrared (MWIR), or intermediate infrared (IIR), spectroscopy has over the years become a technique of choice when specificity is of utmost importance. It has historically been a difficult technique to use for several reasons. First, absorptivities of many materials are quite high in the mid-wavelength infrared region of the electromagnetic spectrum (e.g., from about 3-8 µm) While this is good from the standpoint of sensitivity, it makes sampling sometimes complex. As a result, a wide variety of sampling technologies have been developed to help introduce the sample to the spectrometer in an ideal fashion. A ubiquitous and problematic sample component is water. In the near-infrared (NIR) region, using wavelengths from about 800 nm to 2500 nm, another problem that can arise is the fact that the path length may be too short. One advantage is that near-infrared can typically penetrate much farther into a sample than mid infrared radiation.

One problem faced when using spectroscopy is the fact that many sample preparations contain water. Water has a very high absorbance in the mid-infrared. Therefore, in order to measure a spectrum of water in the classical mid-infrared region of 4000-400 cm$^{-1}$, the path length must be limited to less than a few 10 s of microns. ATR can provide this very small path length needed. In other situations however, the path length of ATR is too small for ideal sampling. This can be the main problem when trying to make measurements through mammalian skin or other biological tissue, or when the desired spectral information is from a deeper depth and not adjacent the surface of the mammalian skin.

Attenuated Total Reflectance (ATR) is often indicated in difficult sampling situations. The spectroscopic usefulness of the effect was first noticed in the 1960s by Fahrenfort and is predictable from basic optical physics. Basically, when light propagates through a medium of high refractive index and approaches an interface with a material of lower refractive index, a transmission and a reflection will occur. The relative strengths of these transmissions and reflections are governed by the Fresnel equations:

$$r_\perp \equiv \frac{E_r}{E_i} = \frac{\frac{n_1}{\mu_1}\cos\theta - \frac{n_2}{\mu_2}\cos\theta'}{\frac{n_1}{\mu_1}\cos\theta + \frac{n_2}{\mu_2}\cos\theta'} \quad (1)$$

$$t \equiv \frac{E_t}{E_i} = \frac{2\frac{n_1}{\mu_1}\cos\theta}{\frac{n_1}{\mu_1}\cos\theta + \frac{n_2}{\mu_2}\cos\theta'} \quad (2)$$

$$r_\| \equiv \frac{E_r}{E_i} = \frac{\frac{n_2}{\mu_2}\cos\theta - \frac{n_1}{\mu_1}\cos\theta'}{\frac{n_1}{\mu_1}\cos\theta' + \frac{n_2}{\mu_2}\cos\theta} \quad (3)$$

$$t_\| \equiv \frac{E_t}{E_i} = \frac{2\frac{n_1}{\mu_1}\cos\theta}{\frac{n_1}{\mu_1}\cos\theta' + \frac{n_2}{\mu_2}\cos\theta} \quad (4)$$

The Fresnel equations give the ratio of the reflected and transmitted electric field amplitude to initial electric field for electromagnetic radiation incident on a dielectric.

In general, when a wave reaches a boundary between two different dielectric constants, part of the wave is reflected and part is transmitted, with the sum of the energies in these two waves equal to that of the original wave. Examination of these equations reveals that when the light is traversing through a high index medium and approaching an interface with a low index medium, the reflected component can be total, with no light being transmitted. The angle at which this occurs is called the critical angle and is defined by the following equation (5):

$$\theta_C = \sin^{-1}\left(\frac{n_2}{n_1}\right) \quad (5)$$

The reflected component has an angle of reflection equal and opposite to the angle of incidence upon the interface. Above the critical angle, all light is reflected. Below the critical angle, some light would transmit through the interface according to the above Fresnel equations. A device operating in this mode would use light that refracts according to Snell's Law (equation (6)):

$$n_1 \sin\theta = n_2 \sin\theta' \quad (6)$$

As previously stated, above the critical angle reflection is total. Fahrenfort first noticed that upon total reflection, a standing, or evanescent, wave is set up at the interface between high and low index. The wave has an exponentially decaying intensity into the rarer (lower index) medium. If an absorbing substance is placed in the vicinity of this evanescent (standing) wave, which extends a distance into the rarer medium, it can absorb portions of the light in specific wavelengths corresponding to the absorption properties of the material. In this way, the total reflection is said to be "frustrated" by the absorption of the sample. The returning light at the detector then is evaluated to determine the missing energy. It follows that this mode can be used to obtain an infrared spectrum of a material in contact with the high index medium through which the light is traveling. The strength of this interaction can be predicted through several equations developed by Harrick. First, the depth of penetration is defined as the 1/e point of the exponential decay of the evanescent (standing) wave (equation (7)):

$$d_p = \frac{\lambda/n_1}{2\pi\left(\sin^2\theta - \left(\frac{n_2}{n_1}\right)^2\right)^{\frac{1}{2}}} \quad (7)$$

where $n_2$ is the sample refractive index and $n_1$ is the crystal refractive index. The depth of penetration is defined as the point at which the strength of the evanescent wave electric vector decays to a value of 1/e (where e is Euler's number) from its original strength. Quick calculations are often done using the depth of penetration to characterize the strength of signal that will be obtained with ATR. The quick calculations may be less accurate but are suitable for providing a guide. A more accurate equation for the point where the evanescent wave electric vector decays was derived by Harrick, namely the effective thickness or effective depth, $d_e$.

An additional complication arises if the sample is thin compared to the 1/e point of the evanescent wave. The effective thickness calculation results in a number that can be used in Beer's Law calculations, and is closely related to the path length in a transmission measurement made at normal incidence. There are now three refractive indices to worry about: $n_1$, the index of the crystal, $n_2$, the index of the thin layer of sample, and $n_3$, the index of whatever is beyond the sample, usually air. Also, since the geometry is usually not near-normal, the calculation must be done for three orthogonal axes. Finally, the measurement is polarization dependent and should be calculated for two orthogonal polarizations. For purposes of this discussion, the thin layer is assumed to by isotropic and the polarization is deemed to be random. So the effective depth equation, for thin layers of sample where the sample layer thickness is much less than the depth of penetration, is as follows:

$$d_e = \frac{1}{\cos\theta} \frac{n_2}{n_1} \frac{d_p}{2} E_{02}^{r2} \cdot \left(\exp\left(-\frac{2z_i}{d_p}\right) - \exp\left(-\frac{2z_f}{d_p}\right)\right) \quad (8)$$

where the z values are the initial and final z-dimension positions of the film relative to the surface of the ATR prism. The E term is the square of the strength of the electric vector in medium 2 E is proportional to light intensity. For polarized incident light $$E_{02,\|}^{r2} = E_{02,x}^{r2} + E_{02,z}^{r2} \quad (9)$$

and $$E_{02,\perp}^{r2} = E_{02,y}^{r2} \quad (10)$$

and this results in $$d_{e,\|} = d_{ex} + d_{ez} \quad (11)$$

and $$d_{e,\perp} = d_{ey} \quad (12)$$

and $$d_{e,random} = (d_{e,\perp} + d_{e,\|})/2 \quad (13)$$

The three orthogonal electric field components are calculated from Fresnel's equations:

$$E_{0x,2}^{r} = \frac{2\cos\theta(\sin^2\theta - n_{31}^2)^{1/2}}{(1 - n_{31}^2)^{1/2}[(1 + n_{31}^2)\sin^2\theta - n_{31}^2]^{1/2}} \quad (14)$$

$$E_{0z,2}^{r} = \frac{2\cos\theta\sin\theta n_{31}^2}{(1 - n_{31}^2)^{1/2}[(1 + n_{31}^2)\sin^2\theta - n_{31}^2]^{1/2}} \quad (15)$$

and $$E_{0y,2}^{r} = \frac{2\cos\theta}{(1 - n_{31}^2)^{1/2}} \quad (16)$$

In the equations immediately above, a thin film approximation is used, in order to greatly simplify the calculation of the field strength. As previously mentioned, Harrick proposed this approximation. The requirement to use this approximation is that the film must be very thin relative to the depth of penetration if the sample were infinitely thick. The depth of penetration for a thick film at 6 µm measuring wavelength would be 2.32 µm. A monolayer of anthrax spores, for example, would have a thickness of approximately 0.4 µm, so the thin film approximation is valid for early detection and identification of anthrax spores deposited onto an ATR prism. The values used in the above equations are as follows: $n_1$=2.2, $n_2$=1.5, $n_3$=1.0, $\theta$=45°, $z_i$=0. and $z_f$=0.4 µm. Calculated values for the field strength are as follows: $E_{0x,2}^{r}$=1.37, $E_{0z,2}^{r}$=0.79, and $E_{0y,2}^{r}$=1.60. Calculated effective path for each vector are $d_{ex}^{iso}$=0.45 µm, $d_{ey}^{iso}$=0.62 µm, $d_{ez}^{iso}$=0.15 µm, $d_{e,\|}^{iso}$=0.60 µm, $d_{e,\perp}^{iso}$=0.62 µm, and $d_{e,random}^{iso}$=0.61 µm. The final value for effective thickness is therefore 0.61 µm.

A single reflection through the ATR system modeled here would give rise to a signal (at 6 µm wavelength) that is comparable to a layer of spores measured in transmission that is 0.61 µm thick, assuming a spore monolayer with a thickness of 0.4 µm. So the ATR technique, even in a single reflection, gives rise to a spectrum with 1.5× the strength of a transmission measurement. This figure can be increased dramatically by using multiple reflections, making ATR infrared an excellent identifier of biological warfare agents such as anthrax.

Other concepts relating to ATR spectroscopy are disclosed in, for example, U.S. Pat. Nos. 6,908,773 to Li et al. for ATR-FTIR Metal Surface Cleanliness Monitoring; 7,218,270 to Tamburino for ATR Trajectory Tracking System (A-Track); 6,841,792 to Bynum et al. for ATR Crystal Device; 6,493,080 to Boese for ATR Measuring Cell for FTIR Spectroscopy; 6,362,144 to Berman et al. for Cleaning System for Infrared ATR Glucose Measurement System (II); 6,141,100 to Burka et al. for Imaging ATR Spectrometer; 6,430,424 to Berman et al. for Infrared ATR Glucose Measurement System Utilizing a Single Surface of Skin.

An often overlooked benefit of the ATR sampling mode for detecting and classifying samples, however, is the immunity to the effects of scatter. Harrick notes that the ATR mode, unlike transmission or regular reflectance, removes the effect of light scatter. Even if a sample is granular in nature, a situation that normally would give rise to light scattering, the ATR spectrum will maintain a flat baseline. This means that different preparations of the same sample can be more similar to each other, and therefore easier to classify in the same group. If there exists real chemical differences between two samples, the differences are more easily discerned because the sample morphology, preparation, and packing are removed as variables. An advantage of ATR, often overlooked, is its immunity to the effects of scatter. A "perfect" infrared spectrum would contain only information related to the molecular structure of the sample. Sampling artifacts almost always are superimposed on this pure spectrum. However ATR can remove some of the differences due to sample scatter, improving the ability to identify and classify a sample. This can be a huge advantage in the area of tissue spectroscopy.

An interesting recurring theme in the spectroscopy literature is the admonition to stay away from the critical angle (Internal Reflection Spectroscopy: Theory and Applications, Francis M. Mirabella, CRC Press, 1993) because spectral distortions will result. This was noted early on in the seminal book by Harrick, and has been repeated many times since. The basis for this warning is seen in the depth of penetration equations listed above. As the angle of incidence gets smaller and approaches the critical angle, the depth of penetration of the evanescent wave into the rarer medium gets larger and larger, up until the critical angle, at which point the total internal reflection condition no longer holds. Below the critical angle, internal reflectance turns into the much more common and much less useful external reflectance. External reflectance is also governed by the laws of Fresnel reflection, but the resulting reflection is no longer total. In external reflection, it is not possible to couple a large efficiency of energy back into the ATR prism and subsequently to the detector.

For many samples, it would be desirable to have a large depth of penetration into the sample. This could be achieved by introducing electromagnetic energy very close to a critical angle for the sample. In most spectrometers, the light beam has a significant angular dispersion, in order to fill the detector and obtain high signal-to-noise ratio (SNR). However, because there is much angular dispersion, as the critical angle is approached, a portion of the beam starts to exceed the critical angle, while another portion of the beam is still at an angle that is well away from the critical angle. In addition, in most samples there is dispersion in the refractive index across the spectral region of interest, and so the critical angle is different for different wavelengths. So these factors require the average angle to often be several degrees away from the critical angle.

It can be readily seen that the depth of penetration into the rarer medium can actually become quite large. There are many applications in which a larger depth of penetration would be desirable. The non-invasive measurement of body constituents is amongst these. The teaching, repeated many times in the literature, is that ATR can not have a large path length and can not have a large depth of penetration, because distortions of the spectrum occur near the critical angle. This problem could be overcome by the use of a highly collimated beam of light. Light sources are now available that can be highly collimated, yet still contain excellent amounts of energy. Many lasers such as quantum cascade lasers and light emitting diode (LED) sources are now available that can be highly collimated and still contain large amounts of energy. But this is not a complete solution to the problem.

Another problem that needs to be overcome is the fact that most samples themselves exhibit wavelength dispersion in their refractive index. If useful spectroscopic information about a sample is desired, whether by fluorescence, near infrared, terahertz, or some other spectroscopy, the signal should be collected over some range of wavelengths. It will almost certainly be true that over the wavelength range of interest, the critical angle will vary with wavelength. The critical angle will even change within the same sample depending on various characteristics of the sample, such as the sample morphology or the physical state of the sample. Therefore it is very difficult, if not impossible to know, a priori, where the critical angle will lie, for a given sample at a given wavelength. What is needed is an added dimension to the ATR measurement, namely that of a mapping of not only intensity versus wavelength, but of intensity versus wavelength versus angle of incidence and/or reflection.

An ATR sampler can be designed that allows for multiple reflections. Multiple reflections thereby multiply the strength of the infrared spectrum. The number of reflections can be adjusted to arrive at an optimum effective path length to give the highest possible signal-to-noise ratio. The apparatuses and methods described here provides for measurements that are at least one, and probably two, orders of magnitude more sensitive than making the measurement in a transmission mode or a traditional ATR mode. In order to successfully map the angular space of interest, it would be desirable to cross over the critical angle and also collect data below the critical angle. This data could be useful in determining a true critical angle for each wavelength.

SUMMARY OF THE INVENTION

An aspect of the invention is directed to an apparatus for detecting the spectral characteristics of a sample. The apparatus comprises an electromagnetic radiation source adapted to excite a sample with electromagnetic radiation; a crystal or prism in communication with the electromagnetic radiation source and the sample, the crystal or prism having a high refractive index adapted to reflect the electromagnetic radiation; a reflector adapted to introduce the electromagnetic radiation to the sample at an angle of incidence at or near a critical angle between the crystal or prism and the sample; and a detector for detecting an electromagnetic radiation from the sample. Additionally the components of the apparatus can be configured to be contained within a housing. Suitable detectors for the apparatus include, but are not limited to, a single element detector, such as a mercury telluride detector, a linear array detector, and a 2-dimensional array detector. The electromagnetic radiation source can be adapted to deliver an electromagnetic radiation to the sample at an angle of incidence which is at or below the critical angle. In other configurations, the electromagnetic radiation delivered to the sample can be delivered such that it approaches and passes the critical angle. In other configurations, the radiation is delivered at an angle at or above the critical angle. This radiation can also be adjusted to be delivered in such a way that it approaches and passes the critical angle. Data processors can also be provided that are in communication with the detector. The data processors can be configured such that the data processor receives information from any of the components of the system and then generates a critical angle map of the sample from one or more electromagnetic radiation detections received by the detector from the sample. Suitable electromagnetic radiation sources include, for example, a quantum cascade laser. In some configurations, the apparatus is adapted to collimate the radiation. The apparatuses are configurable to be housed in an area less than 1 cubic foot in volume, less than 125 cubic inches in volume, and less than 8 cubic inches in volume. Suitable configurations are also adapted to be handheld. In other configurations, a display screen is provided. The display screen can be adapted and configured to display information useful to a user including, for example, the critical angle map. The data processor can be adapted to generate a full map of reflected light intensity versus wavelength versus a mapping of the angle of incidence from the detected electromagnetic radiation. Moreover, in some aspects, a drive mechanism can be provided. The drive mechanism can be adapted to pivot the crystal or prism about an axis. A cooler can also be provided. A cooler would be useful for cooling the detector. Additionally one or more filters can be provided and one or more lenses can be provided. Lenses can be configured to image the electromagnetic radiation onto a detector less that 1 mm squared.

Another aspect of the invention is directed to a method for detecting the spectral characteristics of a sample. The method comprises, for example, placing a sample in proximity to a crystal or prism; emitting an electromagnetic radiation from an electromagnetic radiation source through the crystal or prism; introducing the electromagnetic radiation to the sample through the crystal or prism at an angle of incidence at or near a critical angle of the sample; and detecting an electromagnetic radiation from the sample. Additionally, the method can include the steps of introducing the electromagnetic radiation at an angle of incidence below the critical angle; and increasing the angle of incidence of the electromagnetic radiation incrementally whereby the angle of incidence approaches and passes the critical angle. In some aspects of the method, the method can include the steps of introducing the electromagnetic radiation at an angle of incidence above the critical angle; and decreasing the angle of incidence of the electromagnetic radiation incrementally whereby the angle of incidence approaches and passes the critical angle. Additionally, the method can comprise or more steps of generating a full map of reflected light intensity versus wavelength versus a mapping of the angle of incidence; displaying a generated map; comparing the detected electromagnetic radiation to a database of critical angle measurements; displaying a detected electromagnetic radiation parameter and one or more critical angle measurements from the database; filtering the electromagnetic radiation; pivoting the crystal or prism about an axis; cooling the detector; and imaging the electromagnetic radiation onto a detector area less than 1 mm$^2$.

Still another aspect of the invention is directed to a system for detecting the spectral characteristics of a sample. The system comprises, for example, an electromagnetic radiation source; a crystal or prism in communication with the electromagnetic radiation source and the sample, the crystal or prism having a high refractive index adapted to reflect the electromagnetic radiation internally; and a detector for detecting an electromagnetic radiation from the sample. Additionally the components of the system can be configured to be contained within a housing. Suitable detectors for the system include, but are not limited to, a single element detector, such as a mercury telluride detector, a linear array detector, and a 2-dimensional array detector. The electromagnetic radiation source can be adapted to deliver an electromagnetic radiation to the sample at an angle of incidence which is at or below the critical angle. In other configurations, the electromagnetic radiation delivered to the sample can be delivered such that it approaches and passes the critical angle. In other configurations, the radiation is delivered at an angle at or above the critical angle. This radiation can also be adjusted to be delivered in such a way that it approaches and passes the critical angle. Data processors can also be provided that are in communication with the detector. The data processors can be configured such that the data processor receives information from any of the components of the system and then generates a critical angle map of the sample from one or more electromagnetic radiation detections received by the detector from the sample. Suitable electromagnetic radiation sources include, for example, a quantum cascade laser. In some configurations, the system is adapted to collimate the radiation. The systems are configurable to be housed in an area less than 1 cubic foot in volume, less than 125 cubic inches in volume, and less than 8 cubic inches in volume. Suitable configurations are also adapted to be handheld. In other configurations, a display screen is provided. The display screen can be adapted and configured to display information useful to a user including, for example, the critical angle map. The data processor can be adapted to generate a full map of reflected light intensity versus wavelength versus a mapping of the angle of incidence from the detected electromagnetic radiation. Moreover, in some aspects, a drive mechanism can be provided. The drive mechanism can be adapted to pivot the crystal or prism about an axis. A cooler can also be provided. A cooler would be useful for cooling the detector. Additionally one or more filters can be provided and one or more lenses can be provided. Lenses can be configured to image the electromagnetic radiation onto a detector less that 1 mm squared.

Kits are also contemplated as an aspect of the invention. Suitable kits for detecting the spectral characteristics of a sample, include, for example, an electromagnetic radiation source; and a crystal or prism in communication with the electromagnetic radiation source and the sample, the crystal or prism having a high refractive index adapted to reflect the reflect the electromagnetic radiation. The kits can also include other components, including, but not limited to one or more detectors, filters and/or lenses.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
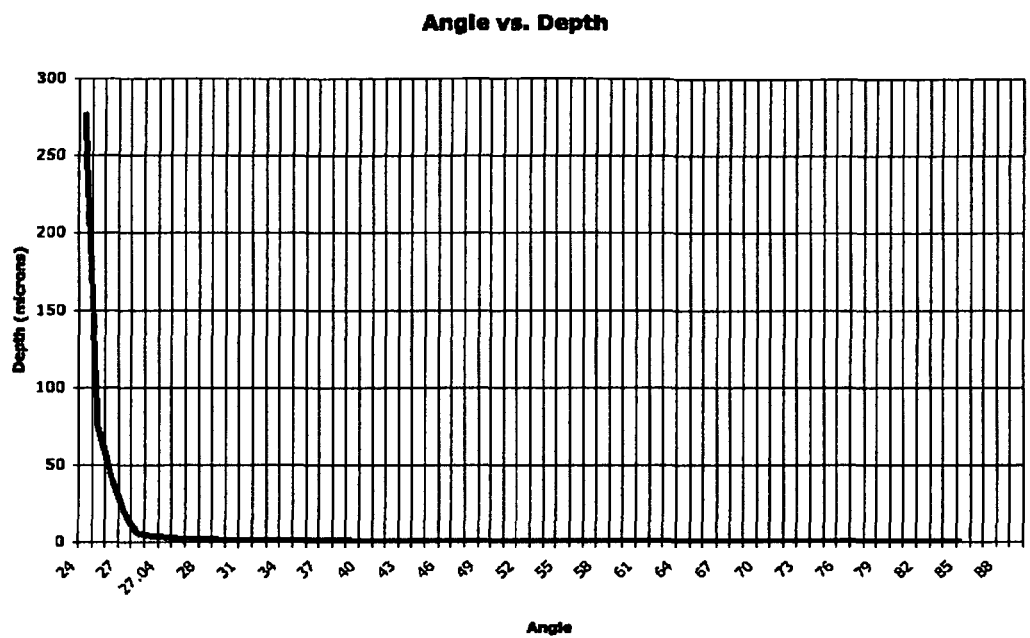
FIG. 1 is a graph showing the correlation between incident angle and the depth of penetration.

This invention therefore is directed toward the creation of devices and systems that generate a critical angle map of a sample in addition to a spectral absorption map. The invention provides an added dimension to the ATR measurement, by providing mapping of not only intensity versus wavelength, but of intensity versus wavelength versus angle of incidence and/or intensity versus wavelength versus angle of incidence reflection. The devices and systems can be configured such that one or more elements or components are formed integrally to achieve a desired physiological, operational or functional result such that the components complete the device. This can be achieved by one or more elements being integrally formed as a single piece or being formed to act in a unified manner. The region around the critical angle is a pen-critical region. Techniques useful to probe the peri-critical region include peri-critical reflectance spectroscopy (PR).

Samples include, but are not limited to biological warfare agent detection, non-invasive transcutaneous detection of glucose, ethanol, cancel cells, and other medically relevant constituents, biomarkers, drug components for new drug discovery, detection of explosives and other harmful chemical agents, early detection of infectious diseases, detection of trace chemical or biological contaminants in drinking water, illegal drug detection, determining the quality of industrial chemicals during production including biofuels such as biodiesel and bioethanol, determining the progress of reactions taking place in bioreactors, in vitro detecting and quantifying constituents of blood such as glucose and creatinine. The maps are generatable with high angular resolution near the critical angle for each wavelength. In most instances, the angular resolution is at least a millidegree or better.

I. Devices And Methods

A peri-critical reflectance spectroscopy apparatus or system, is adapted to provide a source of electromagnetic radiation which can be introduced into a sample, such as those described above. The electromagnetic radiation can be modulated, for example, by an interferometer prior to contacting the sample. The modulated radiation can also be focused by a lens onto a reflective surface, such as a mirror, which then reflects the light into an ATR prism. Furthermore, in some instances, the mirror can be adjusted so that the electromagnetic radiation is introduced to the sample through a range of angles which encompasses a target critical angle. In other words, the electromagnetic radiation is introduced at an angle less than the critical angle and is swept in increments through the critical angle to an angle greater than the critical angle. The mirror can be adjusted to change the angle at which the electromagnetic radiation enters the sample. Alternatively the electromagnetic radiation can be introduced directly to the ATR prism. The electromagnetic radiation, once inside the ATR prism then comes into contact with the sample. The electromagnetic radiation then exits the prism and is detected by a detector and processed by a data processing system.

The critical angle information obtained using the systems and devices described herein is another dimension of information, which is not now obtained with existing technology. A complete map of a sample would therefore be a full map of reflected light intensity versus wavelength versus a mapping of the angle of incidence, at angles that approach and then in fact somewhat cross over, the critical angle. An angular resolution of a few millidegrees (a few microradians) is necessary, because, as illustrated in FIG. 1, the depth of penetration is very sensitive to the angle of incidence around the critical angle. Additionally, a processor can be used with the apparatus to analyze the critical angle data. Once an angular map of the sample is generated by, for example, scanning the sample, the actual angle of the critical angle for the each wavelength can be determined. A spectrum at each wavelength at a constant effective depth can then be plotted.

Figure 2:
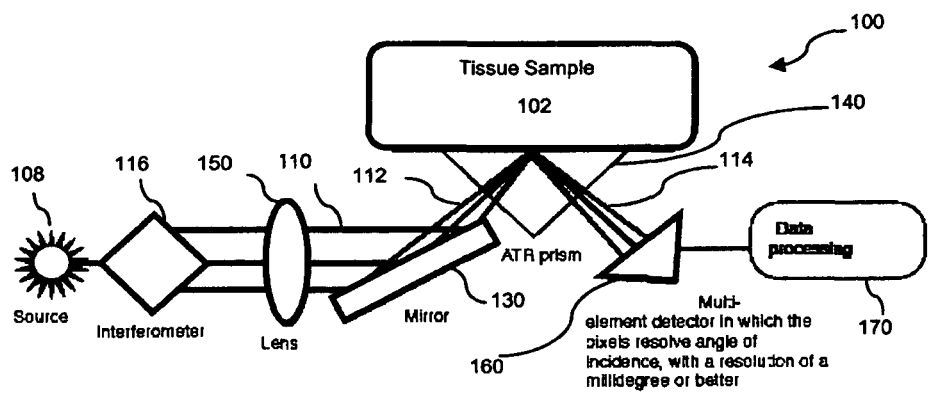
FIG. 2 is an illustration of a peri-critical reflectance spectroscopy system.

FIG. 2 is an illustration of a peri-critical reflectance spectroscopy system. A power source adapted and configured to provide power to a source 108 for electromagnetic radiation or light is adapted to deliver a light beam to an interferometer 116, which separates the beam of light into two or more beams, such as by means of reflection, and thereafter brings the rays together to produce interference. Suitable power sources include, but are not limited to, batteries. As will be appreciated by those skilled in the art, the system can be contained within a suitably designed housing or the components can be configured such that the components function as a housing. The resulting beam 110 then passes through a lens 150, after which it comes in contact with a mirror 130. The mirror reflects the resultant beam 112 through a prism 140 and towards a sample 102. A reflected second beam 114 passes back through the prism 140 where it is received by a multi-element detector 160. The detector can be adapted and configured to resolve an angle of incidence for the pixels to achieve a resolution of a millidegree or better. The resolved pixels are then analyzed using a suitable data processing device or computer. The analysis can include, for example, comparing the data against a library of data to determine a variance of the detected signal to a known sample. Additionally, the system can include a display, such as a liquid crystal display (LCD), adapted to provide a display to a user of the full map of reflected light intensity versus wavelength versus a mapping of the angle of incidence. As will be appreciated by those skilled in the art, connectivity can also be provided which enables the system to sent the information to a printer, or a network. Connectivity can be, for example, wirelessly via the internet as well as via suitable connection ports.

Figure 3:
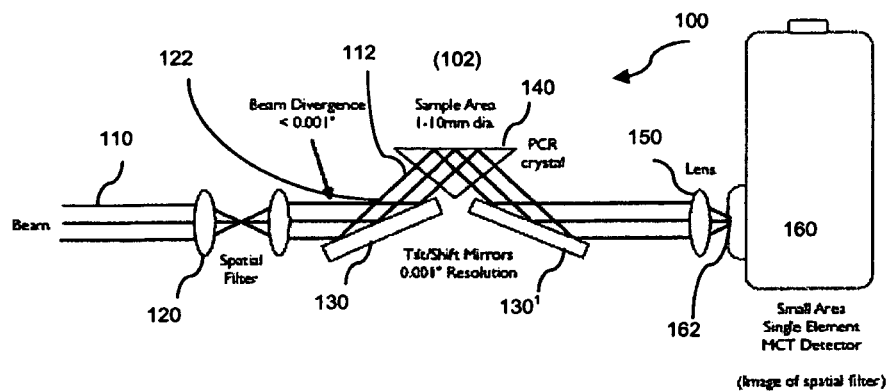
FIG. 3 is an illustration of a peri-critical reflectance spectroscopy system.

As will be appreciated by those skilled in the art, it is not always necessary to measure each angle discretely. The peri-critical reflectance spectroscopy apparatus or system can be constructed as shown in FIG. 3. In FIG. 3, the spectroscopy apparatus 100 is set-up such that the electromagnetic radiation is introduced by a beam 110 to a sample 102 using a mirror 130, such as a tilt/shift mirror having a 0.001 degree resolution. The beam 110 can be delivered to the sample 102 after being passed through a spatial filter 120. Passing the beam 110 through the filter 120 can result in a beam divergence, typically 0.001 degree. After passing through the filter 120, the divergence beam 122 comes in contact with a tilt shift mirror 130 which deflects the beam through a peri-critical reflectance (PR) crystal 140 into the sample 102. Suitable samples can, for example, have a same area as low as 1-10 mm in diameter. After the beam comes in contact with the same, a resulting beam 112 is reflected. The resultant beam 112 can then pass back through the PR crystal 140 to contact a second tilt/shift mirror 130' which transmits the resultant beam 112 through a lens 150 and into a small area single element mercury cadmium telluride (MCT) detector 160.

A peri-critical reflectance (PR) spectroscopy instrument configured as shown in FIG. 3 can include a spatial filter 120 of variable size that allows the infrared (IR) beam having one or more wavelengths from 750 nm to 1000 µm to be collimated to a desired angular resolution. The resulting collimated beam has nearly parallel rays. As a result of collimating, a beam divergence of 1 millidegree is achievable. Launch mirrors 130, 130' can then be configurable such that the mirrors can tilt and shift to vary the angle of incidence on the sample. For example, the angle can be varied in order to cross over a critical angle for all wavelengths. A lens 150 can then be configured to image the spatial filter onto a very small detector area 162. Suitable areas include areas less than 1 mm$^2$, less than 0.01 mm$^2$, and more preferably less than 0.001 mm$^2$. The small area detector enables sensitivity improvement in systems that are limited by detector noise that usually dominate during experiments in the mid-infrared spectroscopy range.

The system can also be adapted and configured such that the mirror remains stationary relative to the sample. In such cases an electromagnetic radiation source with a less collimated beam of energy can be used. Instead of sweeping the beam through a range of angles, the angular measurements can be made using a multiplicity of detectors (arrays) in such a manner such that each detector pixel element senses a progressively smaller (or larger) angle, such angle to include the critical angle at all wavelengths of interest. This detector array is deployed after the sample and needs to be only a linear array of detector elements. Since it is often not possible to know beforehand what the critical angle will be at all of the wavelengths of interest, a detector containing a large number of pixels can be used. Otherwise, as previously described, the entire critical angle space could be mapped by sweeping the beam through different segments or portions of the total critical angle space in need of mapping.

In some instances the detector 160 can be cooled if desired for better sensitivity. Cooling is achievable using a suitable cooling apparatus, means for cooling, or material. For example, cooling with liquid nitrogen may, in some instances, improve sensitivity of the detector. Cooling typically involves decreasing the temperature of the detector semiconductor material to the temperature of liquid nitrogen and most preferably to the temperature of liquid helium.

The beam generated by the system may be an output beam of a Fourier Transform Infrared (FTIR) spectrometer. However, as will be appreciated by those skilled in the art, a beam from a single or series of quantum cascade (QC) lasers may also be used. In some instances, selection of a beam type or source can improve the portability of the devices or systems. Thus, for example, a system less than 1 cubic foot in volume can be transported easily, and a system less than 125 cubic inches in volume can be handheld, and a system less than 8 cubic inches in volume may be concealed and hidden from view. This scalability of size provides significant advantages. Moreover, QC lasers can be highly collimated.

Alternative to using a multi-element detector, the angle of incidence of the beam may be changed manually and successive scans made. The input and the output angle may be changed together in order to obtain a complete map of the spectral data at the entire range of angle of incidences.

The angles interrogated should extend both above and below the expected critical angle. This is because the critical angle varies as a function of wavelength. The goal is to re-create a spectrum as a constant and known degree of closeness to the critical angle, or constant effective depth. In this manner, spectral distortions normally associated with working too close to the critical angle are completely obviated. It is now possible to collect undistorted spectra, while working very close to the critical angle. This allows the ATR method to have longer path length and deeper penetration into the rarer medium (the sample under test) than is possible using conventional methods. This will be particularly important in non-invasive biological measurements and many other measurements such as: detection of low levels of biological warfare agents.

Figure 4:
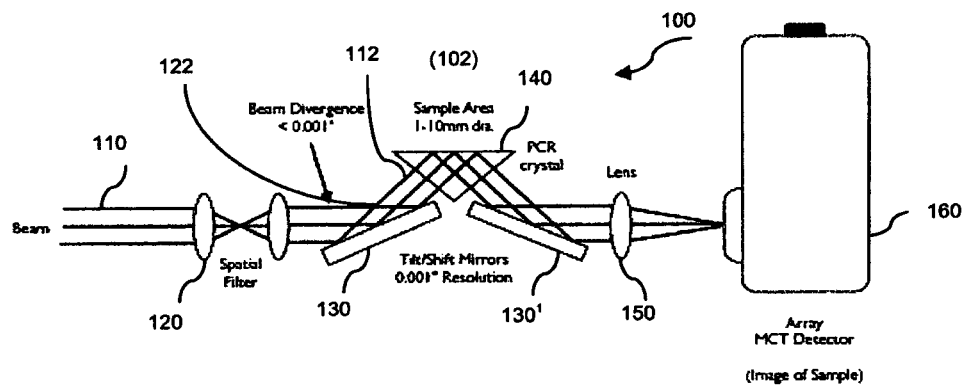
FIG. 4 is an illustration of a peri-critical reflectance spectroscopy system showing imaging capability.

Turning to FIG. 4, an illustration of a peri-critical reflectance spectroscopy system is provided showing imaging capability. In this embodiment, the crystal 140/sample 102 surface is imaged onto an Array MCT detector 160 instead of the spatial filter, as illustrated above. The previous single element detector is replaced with a one- or two-dimensional detector array, as desired. A two-dimensional detector array can be adapted and configured to collect hyperspectral data with one dimension of wavelength, 2 dimensions of image and the further one dimension of angle of incidence. Each of these dimensions can, as will be appreciated by those skilled in the art, have thousands of data points. The depth of profiling capability of this system and technique allows for the creation of a three-dimensional spatial profile of a sample volume with spectral information at each spatial position. The multiple detectors have the effect of reducing the time needed to collect a data set, directly in proportion to the number of detector elements. Additionally a sample 102 area of 1-10 mm in diameter can be used.

Figure 5:
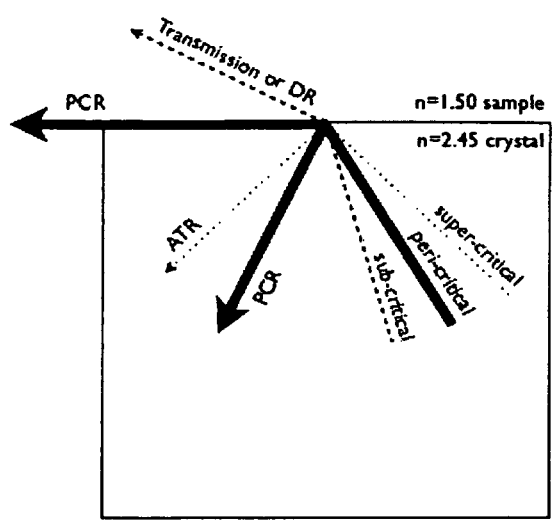
FIG. 5 is graph illustrating different effects achievable by changing an angle of incidence during spectroscopy.

FIG. 5 is graph illustrating different effects achievable by changing an angle of incidence during spectroscopy. Light rays are launched with a high index, or dense medium. Well below the critical angle (sub-critical), light refracts at the crystal/sample interface and then mostly transmits into the sample itself as a propagating wave. If the sample is scattering, then diffuse reflectance (DR) is the result. Well above the critical angle (super critical) light reflects totally and a weak standing or evanescent wave is set up in the rare medium (sample). As a result, no light waves propagate in the sample. The characteristics of the resulting sample spectrum is consistent with attenuated total reflectance (ATR). Immediately in the vicinity of the critical angle (peri-critical), light becomes very sensitive to angle. At the crystal/sample interface, three things happen: light reflects at the negative critical angle, a strong evanescent wave is set-up in the sample, and a traveling wave propagates in a direction parallel to the crystal sample interface plane. This effect benefits peri-critical reflectance (PR) spectroscopy. By resolving angles accurately, to a millidegree, it is possible to map the peri-critical region for all wavelengths and refractive indices present in the given sample and crystal. The reflected PR beam contains strong information about the sample and from deeper depths into the sample than is possible by ATR.

Figure 6:
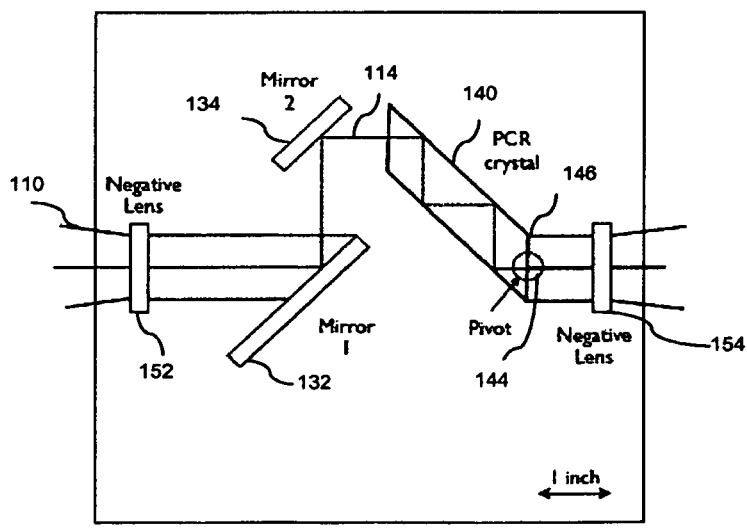
FIG. 6 is an illustration of another pen-critical reflectance spectroscopy system wherein multiple reflections are achievable.

Turning now to FIG. 6, an illustration of another peri-critical reflectance spectroscopy system wherein multiple reflections are achievable is provided. A beam 110 from an electromagnetic radiation source passes through a negative lens 152 and hits a first mirror 132. The beam 110 is deflected from the first mirror 132, forming a resultant beam 112. The resultant beam 112 then hits a second mirror 134 and forms a second resultant beam 114, which comes in contact with a peri-critical reflectance crystal or prism 140. The second resultant beam passes through the PR crystal from which it is then passes through a negative lens 154. Multiple reflections are achieved which are all at or near the critical angle. A precision drive (not shown), or any suitable means to move or rotate the platform, causes a platform to rotate or move. The platform carries first mirror 132, second mirror 134, and the PR crystal 140. The drive enables, for example, the platform to pivot around a pivot point 144 situated at or near an exit face 146 of the crystal 142. The negative lenses 152, 154 allow the instrument to be used in the sample compartment of many FTIR spectrometers that have a focusing beam near the center of the sample compartment. An example of a suitable FTIR device would be any Thermo Nicolet FTIR (Thermo Fisher Scientific, Waltham Mass.). The negative lenses collimate the beam, allowing angular resolution of the resulting collimated beam. Beam divergence, can further be limited by the J-stop (Jacquinot stop or field stop) inside the spectrometer, usually near the source. The beam divergence of the electromagnetic or IR beam is determined by an angular measurement of an increase in beam diameter over a distance from the source, or optical aperture.

Figure 7:
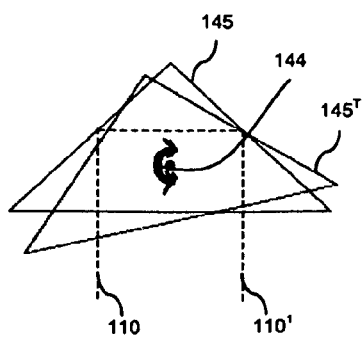
FIG. 7 illustrates a mechanism for changing an angle in a peri-critical reflectance spectroscopy system.

As illustrated in FIG. 7, a mechanism for changing an angle in a peri-critical reflectance spectroscopy system can be achieved. A 45 degree prism 142 made of a high index crystal, such as zinc selenide (ZnSe), can be used. The beam is launched in and out of the bottom face 142' of the prism 142 such that a first beam 110 enters the bottom face 142' of the crystal and a second beam 110' departs the bottom face 142' of the crystal parallel or substantially parallel to the first beam 110. The internal reflections of the beam occur at two facets of the prism following the path illustrated by the dashed line. Thus the incoming first beam 110 perpendicularly enters the bottom face 142' of the crystal, hits a facet of the prism where it is deflected at an angle of 90 degrees. The deflected beam then hits a second facet within the prism where it is deflected a second time at an angle of 90 degrees. The second deflected beam 110' then exits perpendicularly through the bottom face 142' of the crystal such that the incoming first beam 110 and departing second beam 110' are substantially parallel. The prism can be tilted about a pivot point 144. As a result of tilting the prism $142^T$ around the pivot point, the angle of incidence on one facet increases while the angle of incidence on the other facet decreases. The sample under test can be adjacent to, or adhered to, one facet or the other of the prism. The input and output beams remain parallel to each other as the prism tilts. The ability to tilt the crystal while retaining parallel beams minimizes a need for realignment where there is an angle change.

Figure 8:
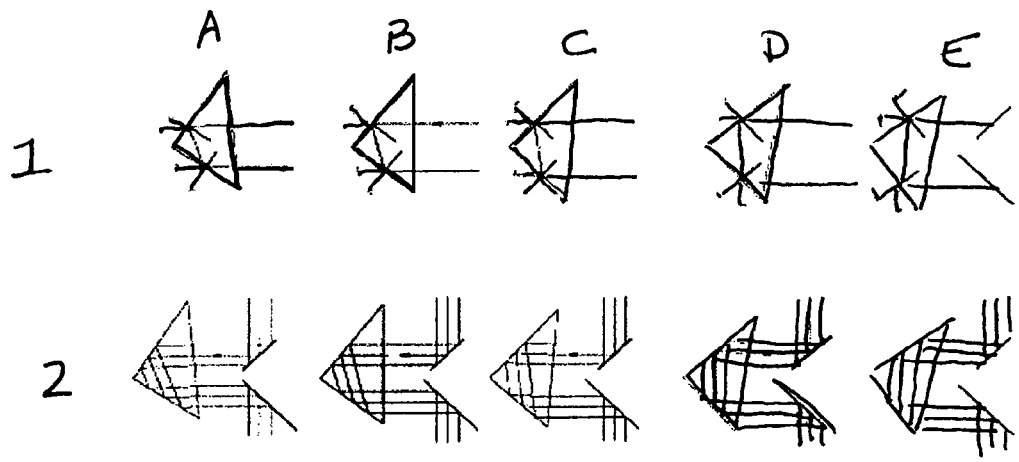
FIG. 8 illustrates a 45 degree prism moving through various angles of incidence.

Turning now to FIG. 8, a 45 degree prism shown on a top line moving through five separate sample angles of incidence (A-E). The prism retains the parallel beams as shown in the bottom line and as described above. Thus, an angular range of up to 10 degrees or more can be useful in PR spectroscopy.

Figure 9:
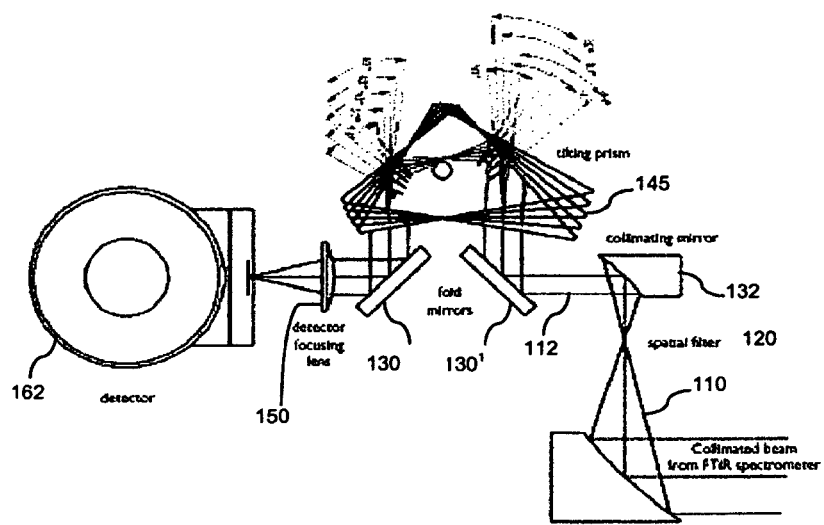
FIG. 9 illustrates an overview of a complete sampling system for spectroscopy.

FIG. 9 illustrates an overview of a complete sampling system for spectroscopy. The sampling system employs the previously described 45 degree prism. In this configuration, a pivot point is found that makes the input and output beams remain stationary during crystal tilting. As will be appreciated by those skilled in the art, the crystal is depicted with long facet and a short facet.

II. Kits

Kits are also contemplated as an aspect of the invention. Suitable kits for detecting the spectral characteristics of a sample, include, for example, an electromagnetic radiation source; and a crystal in communication with the electromagnetic radiation source and the sample, the crystal having a high refractive index adapted to reflect the reflect the electromagnetic radiation. The kits can also include other components, including, but not limited to one or more detectors, filters and/or lenses.

III. EXAMPLES

Example 1

Determining Blood Glucose Levels

The devices and methods described above can be uses to detect levels of glucose. The skin surface of a patient can be placed in proximity to the system. Thereafter, the skin is radiated with an electromagnetic radiation beam through the transmitting crystal. A beam is reflected back out and through the crystal. The return beam carries with it information indicating the blood glucose level in the user. The return beam can be analyzed using a suitable word processor to provide, for example, a full map of reflected light intensity versus wavelength versus a mapping of the angle of incidence. This information can be correlated with other biological parameter information. Additional the map can be displayed on and LCD and/or communicated to a network.

Example 2

Non-Contact Inspection of Materials

Another application is in the area of non-contact inspection. Normally with ATR, it is essential to create a very intimate optical contact between the ATR crystal and the specimen under test. Without this intimate contact, an intermediate layer, usually air, must be considered in the refractive index and depth calculations. With powders and other irregular samples, it is often impossible to remove all of the air space. As a result, the measurement is often unstable from one measurement to the next. The other reason for intimate optical contact is that since the depth of penetration is so small in ATR, the goal is to get the specimen as close to the crystal as possible, where the evanescent field is the strongest. With the present invention, it is possible to make the depth of penetration much larger. Therefore we can get very good spectra even when the specimen is not in physical contact with the ATR crystal. The problem of instability in the region of the evanescent field is thereby avoided. An excellent application of this is in the area of non-contact inspection of materials, especially when the material is moving, for instance on a production line. A particular application in the non-contact inspection field would be the examination of pharmaceutical tablets on a production line.

References

J. Fahrenfort, Spectrochim. Acta 17, 698 (1961).

Harrick, N. J., Internal Reflection Spectroscopy, New York: Wiley Interscience, 1967.

Fringeli U P, Goette J, Reiter G, Siam M, and Baurecht D (1998) Structural Investigations of Oriented Membrane Assemblies by FTIR-ATR Spectroscopy. In Proceedings of the 11th International Conference on Fourier Transform Spectroscopy.

Messerschmidt R G, Multiple Internal Reflectance Spectroscopy System, U.S. Pat. No. 4,730,882 (1988).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for detecting the spectral characteristics of a sample comprising:
    an electromagnetic radiation source adapted to excite the sample with electromagnetic radiation;
    a crystal in communication with the electromagnetic radiation source and the sample, the crystal having a refractive index higher than that of the sample;
    a reflector adapted to introduce the electromagnetic radiation to a measurement site of the sample at a plurality of angles of incidence encompassing a critical angle between the crystal and the sample;
    a detector for detecting electromagnetic radiation from the sample; and a processing device in communication with the detector, the processing device adapted to receive information from the detector obtained at a plurality of angles about the critical angle with millidegree resolution and to identify the intensity of reflected electromagnetic radiation at angles proximate to the critical angle.

2. The apparatus of claim 1 further comprising a housing adapted to contain the electromagnetic radiation source, crystal, reflector and detector.

3. The apparatus of claim 1 wherein the detector is a single element detector.

4. The apparatus of claim 1 wherein the detector is a single element mercury cadmium telluride detector.

5. The apparatus of claim 1 wherein the detector is a linear array detector.

6. The apparatus of claim 1 wherein the detector is a 2-dimensional array detector.

7. The apparatus of claim 1 wherein the electromagnetic radiation source is further adapted to adjust and electromagnetic radiation delivered to the sample to approach and pass the critical angle.

8. The apparatus of claim 1 wherein the processing device is further adapted to generate a critical angle map of the sample from one or more electromagnetic radiation detections received by the detector from the sample.

9. The apparatus of claim 8 further comprising a display screen adapted and configured to display the critical angle map.

10. The apparatus of claim 1 wherein the electromagnetic radiation source is a quantum cascade laser.

11. The apparatus of claim 1 wherein the electromagnetic radiation is collimated.

12. The apparatus of claim 1 wherein the apparatus is less than 1 cubic foot in volume.

13. The apparatus of claim 1 wherein the apparatus is less than 125 cubic inches in volume.

14. The apparatus of claim 1 wherein the apparatus is handheld.

15. The apparatus of claim 1 wherein the apparatus is less than 8 cubic inches in volume.

16. The apparatus of claim 1 wherein the processing device is adapted to generate a full map of reflected light intensity versus wavelength versus a mapping of the angle of incidence from the detected electromagnetic radiation.

17. The apparatus of claim 1 further comprising a drive mechanism adapted to pivot the crystal about an axis.

18. The apparatus of claim 1 further comprising a cooler adapted to cool the detector.

19. The apparatus of claim 1 further comprising a filter.

20. The apparatus of claim 1 further comprising a lens configured to image the electromagnetic radiation onto a detector area less than 1 mm$^2$.

21. A method for detecting the spectral characteristics of a sample comprising:

placing a sample in proximity to a crystal;

introducing electromagnetic radiation from an electromagnetic radiation source to a measurement site of the sample through the crystal at a plurality of angles of incidence encompassing a critical angle of the sample; and detecting electromagnetic radiation from the sample with millidegree resolution about the critical angle.

22. The method of claim 21, wherein the step of introducing electromagnetic radiation comprises:

introducing the electromagnetic radiation at an angle of incidence below the critical angle; and increasing the angle of incidence of the electromagnetic radiation incrementally whereby the angle of incidence approaches and passes the critical angle.

23. The method of claim 22 further comprising the step of generating a full map of reflected light intensity versus wavelength versus a mapping of the angle of incidence.

24. The method of claim 23 further comprising the step of displaying a generated map.

25. The method of claim 22 further comprising the step of comparing the detected electromagnetic radiation to a database of critical angle measurements.

26. The method of claim 25 further comprising the step of displaying data of the detected electromagnetic radiation and one or more critical angle measurements from the database.

27. The method of claim 21, wherein the step of introducing electromagnetic radiation comprises:

introducing the electromagnetic radiation at an angle of incidence above the critical angle; and decreasing the angle of incidence of the electromagnetic radiation incrementally whereby the angle of incidence approaches and passes the critical angle.

28. The method of claim 21 further comprising the step of filtering the electromagnetic radiation.

29. The method of claim 21 further comprising the step of pivoting the crystal about an axis.

30. The method of claim 21 further comprising the step of cooling the detector.

31. The method of claim 21 further comprising the step of imaging the electromagnetic radiation onto a detector area less than 1 mm$^2$.

* * * * *

UNITED STATES PATENT AND TRADEMARK OFFICE
CERTIFICATE OF CORRECTION

PATENT NO.       : 8,730,468 B2
APPLICATION NO. : 12/865698
DATED            : May 20, 2014
INVENTOR(S)      : Robert G. Messerchmidt It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 216 days.

Signed and Sealed this

Twenty-ninth Day of September, 2015

Michelle K. Lee
*Director of the United States Patent and Trademark Office*